United States Patent
Kloke et al.

(10) Patent No.: US 11,986,636 B2
(45) Date of Patent: May 21, 2024

(54) CONTAINERS HAVING CLOSED ENDS, CONTAINER ASSEMBLIES AND MEDICAL DEVICES HAVING SUCH CONTAINERS

(71) Applicant: SCHOTT PHARMA SCHWEIZ AG, St. Gallen (CH)

(72) Inventors: Arne Kloke, St. Gallen (CH); Anil-Kumar Busimi, St. Gallen (CH); Dominique Bauert, St. Gallen (CH)

(73) Assignee: SCHOTT PHARMA SCHWEIZ AG, St. Gallen (CH)

( * ) Notice: Subject to any disclaimer, the term of this patent is extended or adjusted under 35 U.S.C. 154(b) by 292 days.

(21) Appl. No.: 16/945,464

(22) Filed: Jul. 31, 2020

(65) Prior Publication Data
US 2021/0030964 A1    Feb. 4, 2021

(30) Foreign Application Priority Data
Aug. 1, 2019    (EP) .................................... 19189625

(51) Int. Cl.
*A61M 5/24*      (2006.01)
*A61J 1/06*      (2006.01)
*A61M 5/20*      (2006.01)

(52) U.S. Cl.
CPC ........ *A61M 5/2429* (2013.01); *A61M 5/2033* (2013.01); *A61J 1/065* (2013.01); *A61M 2005/247* (2013.01)

(58) Field of Classification Search
CPC .... A61M 5/2429; A61M 5/2033; A61M 5/24; A61M 5/28; A61M 5/285; A61M 5/288;
(Continued)

(56) References Cited

U.S. PATENT DOCUMENTS 2,408,323 A * 9/1946 Lockhart ............. A61M 5/2429
604/203
5,425,715 A 6/1995 Dalling
(Continued)

FOREIGN PATENT DOCUMENTS

| DE | 202010014985 U1 * | 2/2011 | ............. C03C 3/091 |
| EP | 2554201 | 2/2013 | |
| WO | 2012158136 | 11/2012 | |

OTHER PUBLICATIONS

ISO 11608-3, "Needle-based injection systems for medical use—Requirements and test methods—Part 3: Finished containers", Second Edition, Oct. 1, 2012, 16 pages.
(Continued)

*Primary Examiner* — Bradley J Osinski
(74) *Attorney, Agent, or Firm* — Ruggiero McAllister & McMahon LLC

(57) ABSTRACT

Container assemblies for accommodating pharmaceutical compositions are provided. The container assembly includes a container and a plunger. The container has a hollow cylindrical body with an open end and a closed end, which is closed by a bottom portion. The hollow cylindrical body has a length (L), an outer diameter (DO), and an inner diameter with a length to outer diameter ratio between 3:1 and 15:1. The hollow cylindrical body and the bottom portion are formed integrally and of the same material, which is a glass or polymer material. The container has an inner surface with an average Zn-leachability of 0.00085 $\mu g/cm^2$ or less. The plunger is inside the hollow cylindrical body at the open end, is pierceable by a cannula, and is slidable relative to the hollow cylindrical body from the open end towards the closed end.

16 Claims, 2 Drawing Sheets

(58) Field of Classification Search
CPC .. A61M 5/315; A61M 5/32; A61M 2005/247; A61M 5/31511; A61J 1/065
See application file for complete search history.

(56) References Cited

U.S. PATENT DOCUMENTS

| | | | | |
|---|---|---|---|---|
| 5,478,324 | A * | 12/1995 | Meyer | A61M 5/502 604/218 |
| 6,102,896 | A * | 8/2000 | Roser | A61M 5/30 604/218 |
| 7,282,269 | B2 * | 10/2007 | Wang | C08L 51/06 528/901 |
| 7,470,259 | B2 * | 12/2008 | Hoyle, Jr. | A61M 5/2429 604/209 |
| 7,658,724 | B2 * | 2/2010 | Rubin | A61M 5/2033 604/110 |
| 9,682,526 | B2 * | 6/2017 | Julien | B32B 1/08 |
| 10,729,854 | B2 * | 8/2020 | Aneas | A61J 1/16 |
| 2006/0183957 | A1 * | 8/2006 | Forrester | B09B 3/25 588/256 |
| 2012/0130318 | A1 | 5/2012 | Young | |
| 2013/0018311 | A1 | 1/2013 | Denning | |
| 2018/0080586 | A1 * | 3/2018 | Berger | B32B 25/08 |
| 2021/0017070 | A1 * | 1/2021 | Suzuki | A61J 1/1468 |
| 2021/0228806 | A1 * | 7/2021 | Streeter | A61M 5/1782 |

OTHER PUBLICATIONS

ISO 15378, "Primary packaging materials for medicinal products—Particular requirements for the application of ISO 9001:2015, with reference to good manufacturing practice (GMP)", Fourth Edition, Sep. 2017, 92 pages.

DIN EN ISO 10993-17, "Biological evaluation of medical devices—Part 17: Establishment of allowable limits for eachable substances (ISO 10993-17:2002) English version of DIN EN ISO 10993-17:2009-08", Aug. 2009, 36 Pages.

DIN EN ISO 10993-18, "Biological evaluation of medical devices—Part 18: Chemical characterization of materials (ISO 10993-18:2005) English version of DIN EN ISO 10993-18:2009-08", Aug. 2009, 27 pages.

DIN EN ISO 13485, Medical devices—Quality management systems—Requirements for regulatory purposes (ISO 13485:2016); English version EN ISO 13485:2016, English translation of DIN EN ISO 13485:2016-08, Aug. 2016, 91 pages.

Zhou, "Biologics Formulation Factors Affecting Metal Leachables from Stainless Steel", AAPS PharmSciTech, vol. 12, No. 1, Mar. 2011, pp. 411-421.

* cited by examiner

CONTAINERS HAVING CLOSED ENDS, CONTAINER ASSEMBLIES AND MEDICAL DEVICES HAVING SUCH CONTAINERS

CROSS REFERENCE TO RELATED APPLICATIONS

This application claims benefit under 35 USC § 119 of European Application 19189625.7 filed Aug. 1, 2019, the entire contents of which are incorporated herein by reference.

BACKGROUND

1. Field of the Invention

The present invention relates to containers having closed ends, as well as container assemblies for accommodating pharmaceutical compositions, such as compositions of biologics and medical devices having such containers. The container assembly is installable in a medical device, in particular in a medical injector. The invention further relates to a container for accommodating pharmaceuticals and to a medical device for expelling pharmaceuticals.

2. Description of Related Art

Commonly used container assemblies for accommodating pharmaceutical compositions, which are installable in a medical device, are e.g. known from prior art document U.S. Pat. No. 5,425,715 A and are exemplarily shown in FIG. 1. Such prior art container assemblies comprise containers that have a substantially hollow cylindrical body with an open end and an opposite end. The open end is provided for receiving a plunger, while the opposite end has a neck portion with reduced diameter and a flange that is closed by a crimp. For expelling the accommodated pharmaceutical composition by the medical device, the crimp of the container is pierced by a cannula so as to dispense the pharmaceutical therethrough.

However, pharmaceutical compositions accommodated in prior art container assemblies have limited shelf-lives due to leachables or so called extractables migrating into the pharmaceutical composition. More precisely, pharmaceutical compositions accommodated in known container assemblies have a limited shelf-life due to leachables or so called extractables migrating from the container assembly. According to Zhou et al., Biologics Formulation Factors Affecting Metal Leachables from Stainless Steel, AAPS PharmSciTech. 2011 Mar.;12(1):411-21, especially metal leachables are harmful for pharmaceutical compositions stored in the container assemblies, in particular for biologics.

SUMMARY

It is an object of the present invention to provide a container assembly for accommodating pharmaceutical compositions and being installable in a medical device, a corresponding container for accommodating pharmaceutical compositions, and a medical device for expelling pharmaceutical compositions, which overcome the above drawbacks.

It is a further object of the present invention to provide a container assembly for accommodating pharmaceutical compositions and being installable in a medical device, and a corresponding container, which allow for a compact design of the medical device, and to provide a medical device for expelling pharmaceutical compositions, which has a compact size and geometry.

According to a first aspect, the present invention provides a container assembly for accommodating pharmaceutical compositions, in particular biologics. In this description, the term "pharmaceutical composition" refers to a composition that comprises at least a pharmaceutically active agent, and at least one pharmaceutically acceptable excipient, such as a carrier. The pharmaceutically active agent may be a so-called "biological", or "biologic". Biologicals/biologics include proteins, peptides, nucleic acids, vaccines, antibodies, and enzymes. The container assembly is installable in a medical device, in particular in a medical injector or medical injection pen.

The container assembly comprises a container and a plunger. The container can also be referred to as a cartridge, an expelling or injection container or an injection cartridge. The container comprises a hollow cylindrical body having an open end and a dead or closed ("closed") end opposite to the open end. The open end of the container is configured for receiving the plunger that is slidable relative to the hollow cylindrical body from the open end towards the closed end. The closed end is completely closed by a bottom portion. The hollow cylindrical body may have a length between 35 mm and 120 mm, preferably between 42 mm and 70 mm, an outer diameter between 6.85 mm and 30 mm, preferably between 8.65 mm and 22.05 mm, and an inner diameter between 4.65 mm and 27 mm, preferably between 6.85 mm and 19.05 mm, with a length to outer diameter ratio between 3:1 and 15:1, preferably between 3:1 and 12:1, preferably between 3:1 and 10:1, more preferably between 3:1 and 7:1, more preferably between 4:1 and 7:1, more preferably between 5:1 and 7:1 and more preferably between 6:1 and 7:1. The hollow cylindrical body and the bottom portion are formed integrally and of the same material, which is a glass or polymer material. The outer diameter and/or the inner diameter of the hollow cylindrical body can be substantially constant over the entire length of the hollow cylindrical body. With other words, the outer diameter and/or the inner diameter of the hollow cylindrical body does not vary more than 5% over the length of the hollow cylindrical body, respectively, in particular not more than 4%, preferably not more than 3%, more preferably not more than 2%, even more preferably not more than 1%.

The inner surface of the container may have an average Zn-leachability (zinc leachability) of $0.00085 \mu g/cm^2$ or less, preferably $0.00075 \mu g/cm^3$ or less, more preferably $0.00065 \mu g/cm^2$ or less, still more preferably $0.00055 \mu g/cm^2$ or less. The leachability values relate to measurement results from an ICP-MS (inductively coupled plasma mass spectrometry) analysis method. An optional and preferred way of measuring the leachabilities indicated in this description is given in the example section.

The plunger is arrangeable inside the hollow cylindrical body in the region of the open end so as to sealingly close the open end, wherein the plunger is pierceable by a cannula and is slidable relative to the hollow cylindrical body from the open end towards the closed end.

As the hollow cylindrical body and the bottom portion are formed integrally and of the same material, which is a glass or polymer material, the completely closed end of the container is not pierceable by a cannula. Consequently, in the container assembly or a medical device comprising the container assembly with the closed end container, both the plunger actuation for acting upon the accommodated pharmaceutical and the fluidic connection for dispensing the pharmaceutical by a cannula have to be realized via the open end (e.g. by penetrating the plunger with the cannula).

The container assembly according to the present invention provides a solution to effectively increase the shelf-life of pharmaceutical compositions accommodated in the container assembly. Namely, the inventors of the present invention have identified the presence and negative effects of Zn-leachables in prior art containers and container assemblies and have determined that minimizing especially the Zn-leachability to the specified amounts leads to an increased shelf-life of pharmaceuticals stored in the container. Based on this, the container of the present invention provides a solution that is installable in a medical device and minimizes the Zn-leachability, i.e. increase the shelf-life of pharmaceuticals, by a particular feature combination. This feature combination includes an optimized shape and dimensions of the container as well as specific material parameters. Optimal shape and dimensions are achieved by providing the container with a closed end, which allows for a compact size and the specified length and diameter values and ratios, which constitute an optimal balance between favorable inner surface-to-volume ratio and a favorable inner diameter, considering that in a container assembly the inner diameter of the container influences the surface of the rubber plunger in contact with the accommodated pharmaceutical composition. Both the inner surface of the container and the surface of the rubber plunger, which may be in contact with an accommodated pharmaceutical during storage, influence the amount of leachables, such as Zn-leachables, migrating into the accommodated pharmaceutical. Further, the average Zn-leachability of the container material influences the amount of leachables, such as Zn-leachables, migrating into the accommodated pharmaceutical. Hence, the feature combination of the present container including the optimized shape and dimensions and the specific material parameters of the container synergistically contributes to an increase of the shelf-life of pharmaceuticals accommodated in the container.

Further, providing the container with one closed end enables to provide a desired inner volume capacity while reducing the length of the container, and thus of the corresponding container assembly, compared to prior art containers with a neck portion and a crimp. By means of the closed end, the neck portion and the crimp (including a sealing rubber member) can be omitted, which can result in an overall length reduction of more than 5 mm with regard to containers having an inner volume capacity of 1 ml, 1.5 ml or 3 ml and an even greater length reduction with regard to containers having an inner volume capacity of 5 ml to 10 ml. Therefore, the closed end structure of the container and the specific length and diameter values and ratios of the container lead to a compact overall design of the container and the container assembly, which consequently allows to provide a compact design of a corresponding medical device. Further, by omitting the neck portion, the crimp and the sealing rubber member, the number of separate components and materials of the container can be reduced, which reduces manufacturing costs of the container.

In an embodiment of the container assembly, the plunger can comprise a rubber material having a Zn-leachability of $0.00800\mu g/cm^2$ or less, preferably $0.00650\mu g/cm^2$ or less, more preferably $0.00500\mu g/cm^2$ or less, still more preferably $0.00350\mu g/cm^2$ or less. Providing the plunger with a respective rubber material can further increased shelf-life of pharmaceuticals stored in the container by further minimizing the overall amount of Zn migrating into the accommodated pharmaceutical, considering that an inner surface of the plunger is in contact with the accommodated pharmaceutical during storage and use of the container assembly.

The plunger can be entirely or partially be made of the rubber material. In an embodiment, in which the plunger is only partially made of rubber material, the rubber can for example comprise a substantially cylindrical non-rubber component (e.g. thermoplastic, ceramic, glass) with a rubber O-ring, e.g. arranged on a lateral surface of the cylindrical non-rubber component. The substantially cylindrical non-rubber component can comprise the same material as the container or a different material than the container.

Preferably, the plunger can comprise, or essentially consist of, an elastomeric material, such as a rubber. Generally, the elastomeric material may be any suitable elastomer, and more particularly, rubbers constructed from butyl, bromobutyl, chlorobutyl, silicone, nitrile, styrene butadiene, polychloroprene, ethylene propylene diene, fluoroelastomers, thermoplastic elastomers (TPE), and combinations and blends thereof.

In an embodiment, the inner surface of the container assembly can have an average Zn-leachability of $0.00135\mu g/cm^2$ or less, preferably $0.00115\mu g/cm^2$ or less, more preferably $0.00100\mu g/cm^2$ or less, still more preferably $0.00080\mu g/cm^2$ or less. The inner surface of the container assembly comprises the inner surface of the container, i.e. the inner surface of the hollow cylindrical body and of the bottom portion, and the inner surface of the plunger. Thus, providing a material combination that has the specified Zn-leachability can particularly increase shelf-life of pharmaceuticals stored in the container assembly.

In an embodiment, the inner surface of the container assembly can have an average Mg-leachability (magnesium leachability) of $0.04000\mu g/cm^2$ or less, preferably $0.03700\mu g/cm^2$ or less, more preferably $0.03500\mu g/cm^2$ or less, still more preferably $0.03200\mu g/cm^2$ or less. The inventors of the present invention have further identified the presence and negative effects of Mg-leachables in prior art container assemblies and have determined that minimizing also the Mg-leachability to the specified amounts leads to a further increased shelf-life of pharmaceuticals accommodated in the container assembly.

The container assembly can have a pressure compliance F (force) of at least $0.64$ N/mm$^2\times$(inner diameter)$^2$, i.e. of at least $0.64$ N/mm$^2\times$inner diameter$\times$inner diameter. Preferably, the container assembly can have a pressure compliance F (force) of at least $0.75$ N/mm$^2\times$(inner diameter)$^2$, preferably at least $0.8$ N/mm$^2\times$(inner diameter)$^2$, more preferably at least $0.85$ N/mm$^2\times$(inner diameter)$^2$, still more preferably at least $0.9$ N/mm$^2\times$(inner diameter)$^2$, still more preferably at least $0.95$ N/mm$^2\times$(inner diameter)$^2$. The pressure compliance constitutes a minimal axial force that is applyable to the filled container via the plunger, without any leakage occurring on the container assembly. Measurement of the pressure compliance can be performed in accordance with the settings set forth in ISO 11608-3:2012. Such a pressure compliance reduces the risk of damaging the container during use in a medical device, in particular when applying large forces to the container via a plunger, as for example in an epinephrine pen or an emergency drug delivery device. The improved shape and dimensions of the closed-end container contributes to providing the container assembly with the preferred pressure compliance. This applies in particular as the inventors have observed that the leakage mainly occurs at the crimped closure of prior art container assemblies (and not in the region of the plunger). Thus, by replacing the crimped closure with an integral closed end, this weak point can be avoided.

It was found that leachability values can be influenced by the cooling rate used during production of the glass material, e.g. after drawing a glass tube for forming the container. It was found that if the glass undergoes very fast cooling, diffusivity increases whereas hydrolytic, acid resistance and leaching increases. Diffusivity is the susceptibility of the material towards chemical tempering. If the glass cools very slowly, diffusivity decreases, hydrolytic as well as acid resistance increase and leaching is reduced. The effective cooling result can be measured on a given glass article simply by measuring the compaction that a glass article undergoes under controlled temperature conditions, wherein higher compaction corresponds to fast cooling and lower compaction corresponds to slow cooling. Particularly, it was found that desired diffusivity, leaching characteristics, hydrolytic and/or acid resistance values can be obtained, if the glass material used in this invention is produced such that the glass exhibits a compaction of 200 μm/100 mm or less, from 50 to 120 μm per 100 mm length. Preferably, compaction should be in a range of from 60 to 100 μm, or from 65 to 95 μm per 100 mm length.

Such a compaction can be particularly helpful for minimizing Zn-leachability (and other leachability in general, e.g. of Mg, Al), in particular in order to provide the average Zn-leachability of the inner surface of the container of 0.00085μg/cm² or less, preferably 0.00075μg/cm² or less, more preferably 0.00065μg/cm² or less, still more preferably 0.00055μg/cm² or less. Preferably, the material having this compaction can be a glass material.

Compaction measurement is very simple. An article or part of an article (made of the material) of a given length, e.g. a tube or container, or a part thereof, is subjected to heat, wherein the article or part thereof is heated from room temperature to 500° C. by putting the article or part thereof into an oven (pre-heated to 500° C.), kept in the oven at 500° C. for 1 hour, and cooled back to room temperature by taking the article or part thereof out of the oven and letting it cool down at room temperature in ambient atmosphere. Room temperature is 20° C. The length of the article or part thereof is measured before and after heat treatment. The length is the article's diameter or the diameter of its part along its respective longitudinal axis.

According to another embodiment of the invention, the container assembly can comprise 5.00% by weight or less Al2O3, preferably 4.00% by weight or less, more preferably 3.00% by weight or less. The container assembly can preferably comprise more than 0.01% by weight Al2O3, preferably more than 0.10% by weight, more preferably more than 1.00% by weight. In this embodiment, also the Al-leachability can be minimized. This is advantageous as Al-leachables can negatively affect pharmaceuticals, in particular biologics, which are in contact with the material. The inner surface of the container can have an average Al-leachability (aluminum leachability) of 0.01000μg/cm² or less, preferably 0.00700μg/cm² or less, more preferably 0.00500μg/cm² or less, still more preferably 0.00350μg/cm² or less. In an embodiment, the above specified percentages for aluminum may apply for zinc (ZnO) and/or magnesium (MgO). Zinc and magnesium may be present as impurities in many materials.

In an embodiment, the container material, i.e. the material of the hollow cylindrical body and the bottom portion, can be a borosilicate glass or an alumino-silicate glass. Preferably, the material can be a chemically or physically tempered glass. Preferred materials have the following compositional ranges in mol %:

| component | mol % |
|---|---|
| SiO2 | 60 to 85 |
| B2O3 | 3 to 15 |
| Al2O3 | 0 to 5 |
| R2O | 5 to 15 |
| RO | 0 to 10 | wherein R2O means the alkali metal oxides selected from Li2O, Na2O and K2O; and RO means the alkaline earth metal oxides selected from MgO, ZnO, CaO, BaO and SrO.

The material can have an average linear thermal coefficient of expansion α (20° C., 300° C.) of 3 to 11·10-6/K, preferably 3.5 to 7·10-6/K, more preferably about 4.9.10-6/K, a transformation temperature Tg of 400° C. to 700° C., preferably about 565° C., and/or a density ϱ at 25° C. of 2.3 to 2.5 grams (g) per cubic centimeter (cm3), preferably about 2.34 grams (g) per cubic centimeter (cm3).

In an embodiment, the container material, i.e. the material of the hollow cylindrical body and the bottom portion, can be a cycloolefin copolymer (COC) or a cycloolefin polymer (COP).

According to another aspect, the present invention provides a container for accommodating pharmaceutical compositions, in particular biologicals. The container can also be referred to as a cartridge, an expelling or injection container or an injection cartridge. The container is installable in a medical device. The medical device can be a medical injector or medical injection pen, such as an injector for injecting epinephrine (i.e. an epinephrine pen). The medical device can be automatically and/or manually operable. The medical device can be fluidically connected to a dispensing arrangement, such as to a tube of an injection or dispensing arrangement.

The container comprises a hollow cylindrical body having an open end and a closed end opposite to the open end. The open end of the container is configured for receiving a plunger that is slidable relative to the hollow cylindrical body from the open end towards the closed end. The closed end is completely closed by a bottom portion. The hollow cylindrical body may have a length between 35 mm and 120 mm, preferably between 42 mm and 70 mm, an outer diameter between 6.85 mm and 30 mm, preferably between 8.65 mm and 22.05 mm, and an inner diameter between 4.65 mm and 27 mm, preferably between 6.85 mm and 19.05 mm, with a length to outer diameter ratio between 3:1 and 15:1, preferably between 3:1 and 12:1, preferably between 3:1 and 10:1, more preferably between 3:1 and 7:1, more preferably between 4:1 and 7:1, more preferably between 5:1 and 7:1 and more preferably between 6:1 and 7:1. The hollow cylindrical body and the bottom portion are formed integrally and of the same material, which is a glass or polymer material. Thus, the completely closed end of the container is not pierceable by a cannula. Consequently, in a medical device or a container assembly comprising the closed end container, both the plunger actuation for acting upon the accommodated pharmaceutical and the fluidic connection for dispensing the pharmaceutical by a cannula have to be realized via the open end (e.g. by penetrating the plunger with the cannula).

The inner surface of the container may have an average Zn-leachability of 0.00085μg/cm² or less, preferably 0.00075μg/cm² or less, more preferably 0.00065μg/cm² or less, still more preferably 0.00055μg/cm² or less. The leachability values relate to measurement results from an ICP-MS (inductively coupled plasma mass spectrometry) analysis method.

According to another aspect, the present invention provides a medical device for expelling or injecting pharmaceuticals. The medical device can be a medical injector or medical injection pen, such as an injector for injecting epinephrine (i.e. an epinephrine pen). The medical device can be automatically and/or manually operable. The medical device can be fluidically connected to a dispensing arrangement, such as to a tube of an injection or dispensing arrangement.

The medical device comprises a hollow device body and a container assembly, which is installable inside the hollow device body. The container assembly comprises a container and a plunger. The container has a hollow cylindrical body with an open end and a closed end opposite to the open end. The open end is configured for receiving the plunger that is slidable relative to the hollow cylindrical body from the open end towards the closed end, and the closed end is closed by a bottom portion. The hollow cylindrical body may have a length between 35 mm and 120 mm, preferably between 42 mm and 70 mm, an outer diameter between 6.85 mm and 30 mm, preferably between 8.65 mm and 22.05 mm, and an inner diameter between 4.65 mm and 27 mm, preferably between 6.85 mm and 19.05 mm, with a length to outer diameter ratio between 3:1 and 15:1, preferably between 3:1 and 12:1, preferably between 3:1 and 10:1, more preferably between 3:1 and 7:1, more preferably between 4:1 and 7:1, more preferably between 5:1 and 7:1 and more preferably between 6:1 and 7:1. The hollow cylindrical body and the bottom portion are formed integrally and of the same material, which is a glass or polymer material. Preferably, the medical device comprises a container assembly of the type described above.

The medical device further comprises a cannula for expelling or dispensing pharmaceuticals from the container assembly through the cannula, wherein the cannula is arranged so as to pierce the plunger upon actuation of the medical device. Thus, upon actuation, one end of the cannula is introduced through the plunger into the hollow cylindrical body of the container so as to be in contact with the pharmaceutical accommodated in the container. The medical device further comprises an actuation mechanism which is configured to move the container and the plunger relative to each other in a substantially axial direction inside the hollow device body so as to apply pressure to the pharmaceutical accommodated in the container for expelling the pharmaceutical. The actuation mechanism can for example act upon the closed end of the container. The actuation mechanism can for example comprise a spring and/or a motor.

The medical device can further comprise a trigger that is manually operable, wherein the trigger upon operation causes actuation of the actuation mechanism, e.g. by mechanically releasing a retaining or locking mechanism.

In an embodiment, the medical device can have a maximum length that is less than or equal to triple, preferably less than or equal to twice, the length of the hollow cylindrical body of the container. Preferably, the maximum length of the medical device is between 70 mm and 140 mm.

Compared to known medical devices, the medical device according to the invention has a more compact size and design by means of the container assembly comprising the compact closed end container.

All of the leachability values mentioned herein can relate to measurement results from an ICP-MS (inductively coupled plasma mass spectrometry) analysis method, in particular as specified above. The leachability values, i.e. a leachability of X µg/cm$^2$ or less, means that the respective surface or material releases X µg or less of the respective leachable per cm$^2$.

Even though some of the features, functions, embodiments, technical effects and advantages have been described with regard to the container assembly, the container or the medical device, it will be understood that these features, functions, embodiments, technical effects and advantages can also apply accordingly to the container, the container assembly and/or the medical device. Particularly, all preferred embodiments for the container assembly apply also for the container and the medical device and the other way around unless specified otherwise.

An optional and preferred way of measuring the leachabilities indicated in this description is given in the example section.

BRIEF DESCRIPTION OF THE DRAWINGS

For a better understanding of embodiments of the invention and to show how the same may be carried into effect, reference will now be made, by way of example, to the accompanying drawings in which like numerals designate corresponding elements or sections throughout.

DETAILED DESCRIPTION

Examples of embodiments of the present invention will be explained in more detail by virtue of the following embodiments illustrated in the figures and/or described below.

Figure 1:
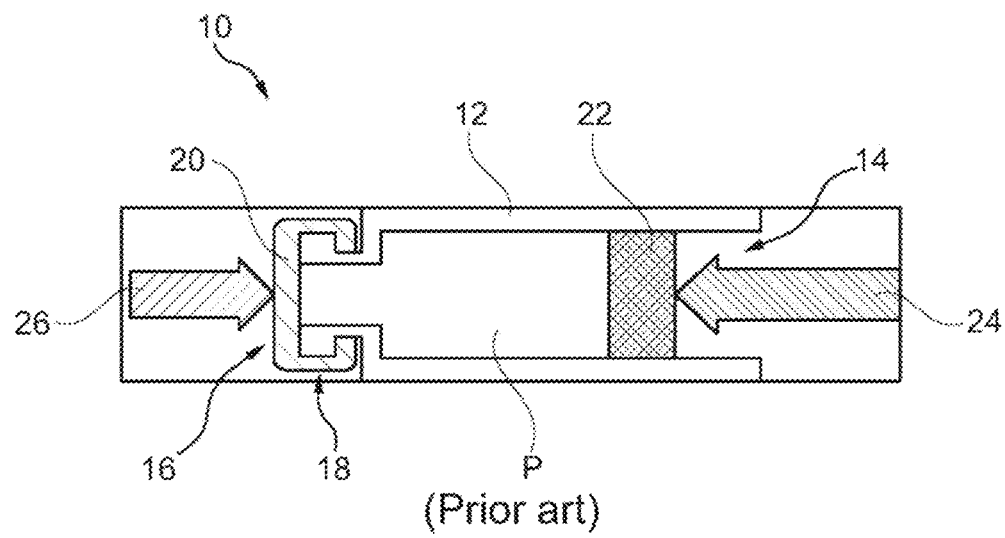
FIG. 1 shows a schematic cross-sectional view of a common prior art container assembly.

FIG. 1 shows a container assembly 10 commonly known from the prior art. The container assembly 10 comprises a container 12 having a body portion with an open end 14 and a closed end 16 opposite to the open end 14. The closed end 16 comprises a neck portion 18 with a reduced diameter and an adjacent flange portion, wherein the flange portion is closed by a metal crimp 20. The container assembly 10 further comprises a plunger 22 that is slidably arranged inside the body portion via the open end 14.

A pharmaceutical P is accommodated in the body portion of the container 12. For expelling or dispensing the pharmaceutical P from the container 12, a plunger actuation 24 (relative to the container 12) and a fluidic connection 26 are provided on opposite sides of the container assembly 10. Upon actuation, the plunger actuation 24 acts on the container assembly 10 and causes expelling of the pharmaceutical P via the opposite fluidic connection 26. The plunger actuation 24 and the fluidic connection 26 are components of a corresponding medical device (not shown in FIG. 1) and are therefore only schematically illustrated by the arrows 24, 26. The fluidic connection 26 is usually a cannula that before or upon actuation of the medical device pierces through the crimp 20 and a subjacent rubber seal (not shown), which rubber seal is arranged between the crimp 20 and the accommodated pharmaceutical P. The container assembly 10 is installable in the corresponding medical device which is therefore designed in accordance with and dependent on the design and configuration of the container assembly 10.

Figure 2:
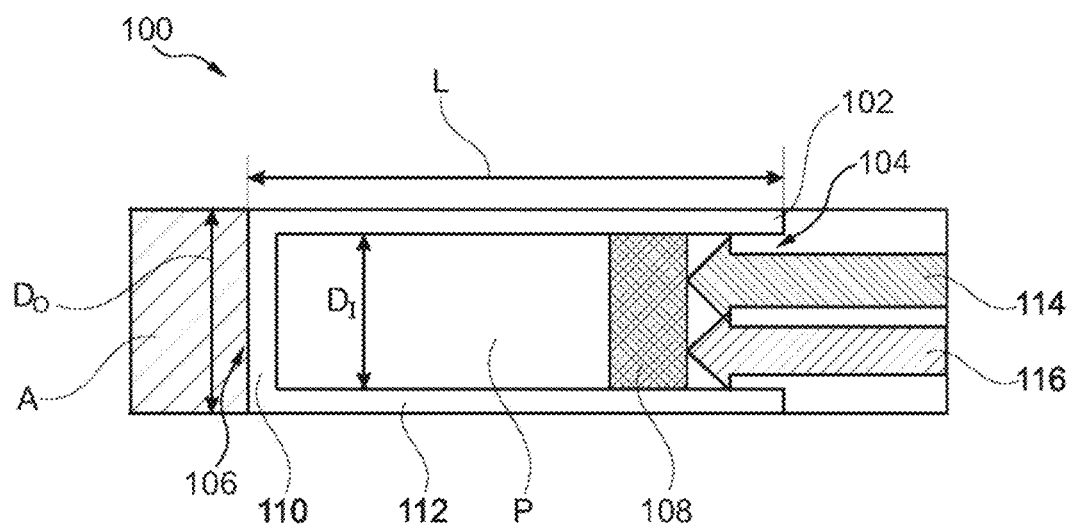
FIG. 2 shows a schematic cross-sectional view of a container assembly according to the present invention.

FIG. 2 shows a schematic cross-sectional view of a container assembly 100 according to an exemplary embodiment of the present invention. The container assembly 100 comprises container 102 having a hollow cylindrical body with an open end 104 and a closed end 106 opposite to the open end 104. The container assembly 100 further comprises a rubber plunger 108. The rubber plunger 108 is received via the open end 104 in the container 102 and is slidable relative to the hollow cylindrical body from the open end 104 towards the closed end 106.

The closed end 106 is closed by a bottom portion 110 which is formed integrally with and of the same material as the hollow cylindrical body, i.e. as the lateral surface 112 (shell surface) of the container 102. In the present example, the container 102, more precisely the lateral surface 112 of the hollow cylindrical body and the bottom portion 110 are made of glass, e.g. borosilicate glass. Alternatively, in other embodiments the container 102 can be made of a polymer. The inner surface of the container 102 has an average Zn-leachability of $0.00085\mu g/cm^2$ or less.

In the example shown in FIG. 2, the hollow cylindrical body of the container 102 has a length L of 45 mm, an outer diameter DO of 15 mm and an inner diameter DI of 12 mm, with a length to outer diameter ratio of 3:1. Alternatively, in other embodiments the container 102 may have a length between 35 mm and 120 mm, preferably between 42 mm and 70 mm, an outer diameter between 6.85 mm and 30 mm, preferably between 8.65 mm and 22.05 mm, and an inner diameter between 4.65 mm and 27 mm, preferably between 6.85 mm and 19.05 mm, with a length to outer diameter ratio between 3:1 and 15:1, preferably between 3:1 and 12:1, preferably between 3:1 and 10:1, more preferably between 3:1 and 7:1, more preferably between 4:1 and 7:1, more preferably between 5:1 and 7:1 and more preferably between 6:1 and 7:1.

A pharmaceutical P is accommodated in the hollow cylindrical body of the container 102. For expelling or dispensing the pharmaceutical P from the container 102, both a plunger actuation 114 (relative to the container 102) and a fluidic connection 116 are realized on the same side of the container 102, i.e. at the open end 104 of the container 102. The plunger actuation 114 and the fluidic connection 116 are components of a corresponding medical device (shown in FIG. 3) and are therefore only schematically illustrated by the arrows 114, 116 in FIG. 2. The fluidic connection 116 can be a cannula that upon actuation of the medical device pierces through the rubber plunger 108. Further, upon and during actuation, the container 102 is moved axially relative to the plunger 108 and the fluidic connection 116.

By providing the container 102 with a closed end in contrast to the prior art crimp assembly, the neck portion, the flange, the rubber seal and the crimp can be omitted. Thus, the container 102 comprises less components than the prior art assembly and has a more compact size and shape. The dashed area A shown in FIG. 2 represents the overall volume reduction in a corresponding medical device that can be gained by the container 102 according to the present invention compared to the prior art crimp-type container.

Figure 3:
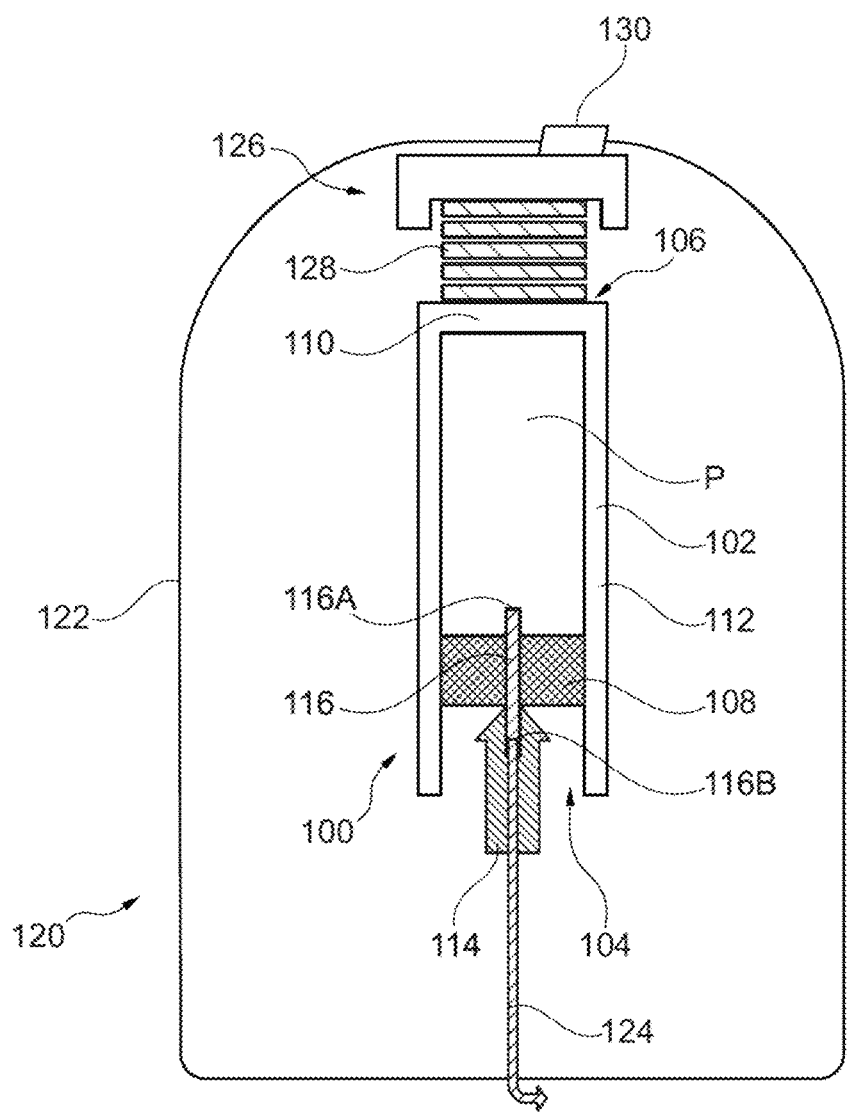
FIG. 3 shows a schematic cross-sectional view of a medical device according to the present invention comprising the container assembly of FIG. 2.

The container assembly 100 is installable in a medical device. A medical device 120 according to an exemplary embodiment of the present invention is schematically shown in FIG. 3. The medical device 120 comprises a hollow device body 122 (a device housing), in which the container assembly 100 and further components of the medical device 120 are housed. Same reference signs are used throughout the figures for the same or mutually corresponding elements and features.

As shown in FIG. 3 the fluidic connection 116 is a cannula that pierces through the plunger 108 and extends with a first end 116A into the hollow cylindrical body of the container 102. An opposite second end of the cannula is fluidically connected to a tube 124 for expelling the pharmaceutical P accommodated in the container 102 via the cannula and the tube 124. The tube 124 can be fluidically connected to further components of the medical device 120 or a connected device.

In the example of FIG. 3, the plunger actuation 114 relative to the container 102, more precisely the movement of the container 102 relative to the plunger 108 is realized by the actuation mechanism 126. The actuation mechanism 126 comprises a spring 128, which in an initial position (unactuated state) is preloaded. The actuation mechanism 126 further comprises a trigger 130. Upon actuation of the medical device 120 by operating the trigger, the spring 128 applies force to and thus moves the container 102 relative to the plunger 108 and relative to the cannula 116. The plunger 108 and the cannula 116 maintain stationary during actuation and use of the medical device 120. By moving the container 102 relative to the stationary plunger 108, the plunger 108 applies pressure to the accommodated pharmaceutical P, which is thus expelled via the cannula 116 and the fluidically connected tube 124.

EXAMPLE

For analyzing the average leachability by means of ICP-MS, portions of test and control extracts can be prepared in suitable plastic containers and can be acidified to approximately 2% with concentrated nitric acid. The resulting solutions can be analyzed with the following method and instrumental parameters:

TABLE 1

| ICP-MS; Instrumental Parameters | |
|---|---|
| Timing Parameters | |
| Sweeps/Readings | 20 |
| Readings/Replicate | 1 |
| Number of Replicates | 3 |
| Signal Processing | |
| Detector Mode | Dual |
| AutoLens | On |
| Spectral Peak Processing | Average |
| Signal Peak Processing | Average |
| Blank Subtraction after internal standard | |
| Pump Parameters | |
| Sample Analysis Speed | 24 mL/min |
| Sample Flush Time | 80-120 sec |
| Sample Flush Speed | 48 mL/min |
| Read Delay Time | 30-45 sec |

TABLE 2

| ICP-MS; Ion Mass Used for Analysis | |
|---|---|
| Element | Mass |
| Mg | 24 |
| Al | 27 |
| Zn | 66 |

Based on the above method and instrumental settings and parameters, an ICP-MS analysis has been conducted. The purpose of this analysis was to perform a chemical characterization of a glass container according to an embodiment of the invention. Per ISO 10993-18:2009, the chemical characterization information generated was used for measurement of the level of a leachable substance in a medical device in order to allow the assessment of compliance with the allowable limit derived for that substance from health based risk assessment (ISO 10993-17:2009).

This analysis was conducted based on ISO 10993-18, Biological evaluation of medical devices—Part 18: Chemical characterization of materials. The analysis was performed in compliance with the ISO 13485:2016 standard.

The test article was prepared based on a surface area of 27.4 cm² for one glass cartridge. Only the glass cartridge was included in the preparation. The plunger was removed. The test article was not subdivided.

The analytical extraction was prepared according to TABLE 3:

TABLE 3

Analytical Extraction

| Vehicle | Extraction Ratio | Article Amount (cm²) | Pieces of Test Article | Volume of Vehicle (mL) | Extraction Condition | Number of Cycles | Final Volume (mL) |
|---|---|---|---|---|---|---|---|
| Purified Water Extraction prepared in a suitable plastic container for ICP-MS testing. | 3 cm²:1 mL | 54.8 | 2 | 18 | 50° C. for 72 hours | 1 | 18 |

System suitability standards were prepared in 2% nitric acid and diluted to result in final concentrations of 10, 250, 500 and 750 ng/mL. These standard solutions were analyzed and the resulting responses evaluated for system suitability criteria prior to examining the test extract results.

Portions of the test and control extracts prepared in suitable plastic containers were acidified to approximately 2% with concentrated nitric acid. The resulting solutions were analyzed with the above method and instrumental parameters.

The same ICP-MS analysis was performed for a commercially available prior art glass container with the structural configuration shown in FIG. 1.

A comparison of the measured values of the glass container according to the invention and the commercially available prior art glass container is shown in the TABLE 4 below.

TABLE 4 comparison of test results for a glass container of the invention and a prior art glass container

| | Zn-leachability μg/test article | Mg-leachability μg/test article | Al-leachability μg/test article |
|---|---|---|---|
| glass container according to the invention | <0.00400 | <0.00400 | <0.00400 |
| prior art glass container | 0.02580 | 0.41100 | ./. |

LIST OF REFERENCE SIGNS

| P | pharmaceutical | 10 | container assembly (prior art) |
| 100 | container assembly | 12 | container (prior art) |
| 102 | container | 14 | open end (prior art) |
| 104 | open end | 16 | closed end (prior art) |
| 106 | dead end | 18 | neck portion (prior art) |
| 108 | plunger | 20 | crimp (prior art) |
| 110 | bottom portion | 22 | plunger (prior art) |
| 112 | lateral surface | 24 | plunger actuation (prior art) |
| 114 | plunger actuation | 26 | fluidic connection (prior art) |
| 116 | fluidic connection (cannula) | | |
| 116A | first end of the cannula | | |
| 116B | second end of the cannula | | |
| L | length | | |
| Do | outer diameter | | |
| Di | inner diameter | | |
| 120 | medical device | | |

-continued

LIST OF REFERENCE SIGNS

| 122 | hollow device body (device housing) |
| 124 | tube |
| 126 | actuation mechanism |
| 128 | spring |
| 130 | trigger |

What is claimed is:

1. A container assembly for accommodating pharmaceutical compositions, comprising:
a container having a hollow cylindrical body having a constant outer diameter along its length with an open end and a closed end opposite to the open end, the closed end being closed by a bottom portion, the hollow cylindrical body and the bottom portion being formed integrally and of a common material, which is a glass or polymer material, the hollow cylindrical body having a length (L) between 35 mm and 120 mm, an outer diameter (Do) between 8.65 mm and 30 mm, and an inner diameter (Di) between 4.65 mm and 27 mm;
a length to outer diameter ratio between 3:1 and 15:1;
an inner surface of the container having an average Zn-leachability of 0.00135 μg/cm² or less; and
a solid plunger having no holes or empty spaces within and having a length, a first surface, a second surface and a perimeter along the length with an outer surface in the open end to sealingly close the inner surface of the open end to define sealed area, wherein the solid plunger is pierceable by a cannula and is slidable on the inner surface from the open end towards the closed end, and wherein the outer surface of the perimeter of the solid plunger completely contacts the inner surface of the hollow cylindrical body.

2. The container assembly of claim 1, wherein the inner surface of the container has an average Zn-leachability is 0.00085 µg/cm2 or less.

3. The container assembly of claim 1, wherein the inner surface has an average Mg-leachability of 0.04000 µg/cm$^2$ or less.

4. The container assembly of claim 1, further comprising a pressure compliance of at least 0.64 N/mm$^2$ ×(inner diameter)$^2$.

5. The container assembly of claim 1, wherein the common material has a compaction of 200 µm/100 mm or less.

6. The container assembly of claim 1, wherein the common material is selected from a group consisting of a borosilicate glass, an alumino-silicate glass, a cycloolefin copolymer, and a cycloolefin polymer.

7. A medical device for expelling or injecting pharmaceutical compositions, comprising:
a hollow device body having a cannula;
a container assembly inside the hollow device body, the container assembly comprising:
a container having a hollow cylindrical body having a constant outer diameter along its length with an open end and a closed end opposite to the open end, the closed end being closed by a bottom portion, the hollow cylindrical body and the bottom portion being formed integrally and of a common material, which is a glass or polymer material, the hollow cylindrical body having a length (L) between 35 mm and 120 mm, an outer diameter (Do) between 8.65 mm and 30 mm, and an inner diameter (Di) between 4.65 mm and 27 mm;
a length to outer diameter ratio between 3:1 and 15:1;
an inner surface of the container having an average Zn-leachability of 0.00135 µg/cm$^2$ or less; and
a solid plunger having no holes or empty spaces within and having a length, a first surface, a second surface and a perimeter along the length with an outer surface in the open end to sealingly close the inner surface of the open end to define a sealed area, wherein the solid plunger is slidable on the inner surface from the open end towards the closed end, and wherein the outer surface of the perimeter of the solid plunger completely contacts the inner surface of the hollow cylindrical body; and
an actuation mechanism that moves the container and the solid plunger relative to each other and relative to the cannula in a substantially axial direction inside the hollow device body, the container assembly being arranged in the hollow device body so that the cannula pierces the solid plunger into the sealed area upon movement by the actuation mechanism and applies pressure to the sealed area.

8. The medical device of claim 7, further comprising a pharmaceutical composition in the sealed area.

9. The medical device of claim 7, wherein the common material has a compaction of 200 µm/100 mm or less.

10. The medical device of claim 7, wherein the common material is selected from a group consisting of a borosilicate glass, an alumino-silicate glass, a cycloolefin copolymer, and a cycloolefin polymer.

11. The medical device of claim 7, wherein the solid plunger comprises a rubber material having a Zn-leachability of 0.00800 µg/cm$^2$ or less.

12. The medical device of claim 7, wherein the container has an inner surface that has an average Zn-leachability is 0.00085 µg/cm$^2$ or less.

13. The medical device of claim 7, wherein the container has and inner surface that has an average Zn-leachability is 0.00055 µg/cm$^2$ or less.

14. The medical device of claim 7, wherein the inner surface has an average Mg-leachability of 0.04000 µg/cm$^2$ or less.

15. The medical device of claim 7, further comprising a pressure compliance of at least 0.64 N/mm$^2$ ×(inner diameter)$^2$.

16. The medical device of claim 7, wherein the length to outer diameter ratio is between 6:1 and 7:1.1.

\* \* \* \* \*